US012630491B2

(12) United States Patent
Janka et al.

(10) Patent No.: US 12,630,491 B2
(45) Date of Patent: May 19, 2026

(54) PRODUCTION OF 2,2,4,4-TETRAMETHYLCYCLOBUTANE-1,3-DIOL FROM SECONDARY ALCOHOLS AND 2,2,4,4-TETRAMETHYLCYCLOBUTANEDIONE USING HOMOGENEOUS CATALYSTS

(71) Applicant: Eastman Chemical Company, Kingsport, TN (US)

(72) Inventors: Mesfin Ejerssa Janka, Kingsport, TN (US); Robert Thomas Hembre, Johnson City, TN (US); Scott Donald Barnicki, Kingsport, TN (US); Robert Sterling Kline, Kingsport, TN (US); Stephanie Rollins Testerman, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 396 days.

(21) Appl. No.: 18/250,581

(22) PCT Filed: Nov. 30, 2021

(86) PCT No.: PCT/US2021/061085

§ 371 (c)(1),
(2) Date: Apr. 26, 2023

(87) PCT Pub. No.: WO2022/119793

PCT Pub. Date: Jun. 9, 2022

(65) Prior Publication Data

US 2023/0406792 A1 Dec. 21, 2023

Related U.S. Application Data

(60) Provisional application No. 63/199,052, filed on Dec. 4, 2020.

(51) Int. Cl.
*C07C 29/143* (2006.01)
*B01J 31/22* (2006.01)

(52) U.S. Cl.
CPC ............. *C07C 29/143* (2013.01); *B01J 31/22* (2013.01); *B01J 2531/821* (2013.01); *C07C 2531/28* (2013.01)

(58) Field of Classification Search
CPC .... C07C 29/143; B01J 31/22; B01J 2531/821
See application file for complete search history.

(56) References Cited

U.S. PATENT DOCUMENTS

| | | | | |
|---|---|---|---|---|
| 8,420,868 | B2 * | 4/2013 | Liu | C07C 29/145 568/839 |
| 9,238,602 | B1 | 1/2016 | Stavinoha, Jr. et al. | |
| 9,238,603 | B1 | 1/2016 | Stavinoha, Jr. et al. | |
| 9,533,928 | B2 | 1/2017 | Dong et al. | |
| 9,988,329 | B1 * | 6/2018 | Janka | B01J 23/8878 |
| 10,099,978 | B2 * | 10/2018 | Chan | B01J 37/08 |
| 2008/0132738 | A1 | 6/2008 | McCusker-Orth et al. | |
| 2012/0149946 | A1 | 6/2012 | Liu et al. | |
| 2017/0334815 | A1 | 11/2017 | Chan et al. | |

FOREIGN PATENT DOCUMENTS

| | | | |
|---|---|---|---|
| CN | 103694083 | A | 4/2014 |
| CN | 105732329 | B | 10/2018 |
| CN | 110124674 | A | 8/2019 |
| CN | 111423307 | A | 7/2020 |
| CN | 111875487 | A | 11/2020 |
| CN | 112047834 | A | 12/2020 |
| CN | 110105186 | B | 4/2022 |
| CN | 111905755 | B | 7/2022 |
| CN | 112023919 | B | 7/2022 |
| CN | 112023939 | B | 7/2022 |
| CN | 110170280 | | 9/2022 |
| CN | 112047813 | B | 12/2022 |
| CN | 112174797 | B | 12/2022 |
| CN | 112079700 | B | 3/2023 |
| WO | WO 2018 148092 | A1 | 8/2018 |

OTHER PUBLICATIONS

Co-pending U. S. U.S. Appl. No. 18/250,587, filed Apr. 26, 2023; Janka and Hembre; now U. S. Publication No. 2023-0399278.

Notification of Transmittal of the International Search Report and the Written Opinion of the International Searching Authority, or the Declaration date of mailing Mar. 9, 2022 received in International Application No. PCT/US2021/061083.

Notification of Transmittal of the International Search Report and the Written Opinion of the International Searching Authority, or the Declaration date of mailing Mar. 9, 2022 received in International Application No. PCT/US2021/061085.

Madeleine C. Warner, Charles P. Casey, Jan E. Bäckvall "Shvo's Catalyst in Hydrogen Transfer Reactions" Top. Organomet. Chem. 37, pp. 85-125 (2011).

Menashe, Naim and Shvo, Youval; "Catalytic Disproportionation of Aldehydes with Ruthenium Complexes"; Organometallics, vol. 10, 1991, pp. 3885-3891.

Yigal Blum and Youval Shvo "Catalytically Reactive Ruthenium Intermediates in the Homogeneous Oxidation of Alcohols to Esters." Isr. J. Chem. 24, pp. 144-148 (1984).

Yigal Blum, Youval Shvo and Daniel F. Chodosh "Structure of (□4-Ph4C5CO)(CO)3Ru—a Catalyst Precursor in Hydrogen Transfer and Dehydrogenation Reactions of Alcohols" Inorg. Chim Acta 97, pp. L25-L26 (1985).

* cited by examiner

*Primary Examiner* — Sikarl A Witherspoon
(74) *Attorney, Agent, or Firm* — Tammye L. Taylor Polk

(57) ABSTRACT

Disclosed is a process for preparing 2,2,4,4-tetramethylcyclobutane-1,3-diol by reacting 2,2,4,4-tetramethylcyclobutanedione with a secondary alcohol in the presence of a transfer hydrogenation catalyst.

20 Claims, 2 Drawing Sheets

PRODUCTION OF 2,2,4,4-TETRAMETHYLCYCLOBUTANE-1,3-DIOL FROM SECONDARY ALCOHOLS AND 2,2,4,4-TETRAMETHYLCYCLOBUTANEDIONE USING HOMOGENEOUS CATALYSTS

CROSS-REFERENCE TO RELATED APPLICATION(S)

This application is a national stage filing under 35 USC § 371 of International Application Number PCT/US2021/061085, filed on Nov. 30, 2021 which claims the benefit of the filing date to U.S. Provisional Application No. 63/199,052, filed on Dec. 4, 2020, the entire disclosures of which are incorporated by reference herein.

FIELD OF THE INVENTION

This disclosure generally relates to a homogeneous catalytic process for preparing 2,2,4,4-tetramethylcyclobutane-1,3-diol (TMCD) by reacting 2,2,4,4-tetramethylcyclobutanedione (dione) with a secondary alcohol.

BACKGROUND OF THE INVENTION

Conventionally, 2,2,4,4-tetramethylcyclobutane-1,3-diol (TMCD) can be produced by the hydrogenation of 2,2,4,4-tetramethylcyclobutanedione (dione) using a heterogeneous catalyst.

In this conventional process, TMCD can be produced by (i) conversion of isobutyric acid to isobutyric anhydride, (ii) converting isobutyric anhydride to dione, and (iii) hydrogenation of dione to TMCD.

In this conventional process, hydrogen is required. This process operates at relatively high pressure of hydrogen and suffers from the production of a number of byproducts, some produced by acid-catalyzed cyclobutane ring-opening during the hydrogenation process.

In the present disclosure a new process is disclosed that uses a ruthenium-containing homogeneous catalyst in a transfer hydrogenation (TH) reaction to give highly selective reduction of dione, along with the coproduction of a ketone using a dione and a secondary alcohol as raw materials. In contrast the traditional TH heterogeneous catalysts do not promote this transformation.

This new TH process can provide an effective alternative to traditional hydrogenation (with $H_2$) for the conversion of dione to TMCD. This new process provides the following benefits: (1) this TH process is an inherently safer process (low pressure and does not use $H_2$, which is an explosion hazard), (2) cost savings from a reduction in $H_2$ usage, (3) lower associated capital costs, (4) significantly lower byproducts and thus higher yields. With lower byproducts, TMCD refining can be simplified significantly, with less purging required.

The present disclosure addresses these unmet needs as well as others, which will become apparent from the following description and the appended claims.

SUMMARY OF THE INVENTION

The process of the present disclosure is as set forth in the appended claims.

One embodiment of the present disclosure is a process for the producing 2,2,4,4-tetramethylcyclobutane-1,3-diol comprising:

(i) contacting 2,2,4,4-tetramethylcyclobutanedione with a secondary alcohol in the presence of a transfer hydrogenation catalyst to produce 3-hydroxy-2,2,4,4-tetramethylcyclobutanone (ketol) and the corresponding ketone derived from the secondary alcohol; and (ii) contacting the 3-hydroxy-2,2,4,4-tetramethylcyclobutanone with a secondary alcohol in the presence of a transfer hydrogenation catalyst to produce 2,2,4,4-tetramethylcyclobutane-1,3-diol and the corresponding ketone derived from the secondary alcohol, wherein the ketone is optionally removed by reactive distillation.

In one embodiment, the transfer hydrogenation catalyst is a ruthenium complex compound.

In one embodiment, the transfer hydrogenation catalyst is one or more of $H_2Ru(PPh_3)_4$, $Ru_3(CO)_{12}$, $(Ar_4C_4CO)Ru(CO)_3$ and $(Ar_4C_4CO)_2H(\mu\text{-}H)(CO)_4Ru_2$, wherein $(Ar_4C_4CO)Ru(CO)_3$ is represented by the general formula:

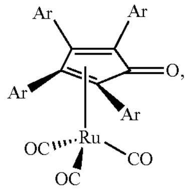

and Ar is represented by the general formula:

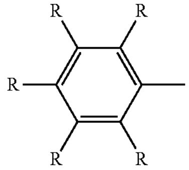

and the groups R are the same or different and are selected from H, methyl, ethyl, or a linear or branched alkyl group containing from 3 to 10 carbon atoms, substituted or unsubstituted aromatic group, a carbonyl-containing group such as an ester or amido group with 2-12 carbon atoms, an amino group with 2-12 carbon atoms, alkoxy with 3-10 carbon atoms, a nitrile, fluoro, trifluoromethyl or fluorinated hydrocarbon group such as perfluorobutyl or pentaflurophenyl;

and wherein $(Ar_4C_4CO)_2H(\mu\text{-}H)(CO)_4Ru_2$ is represented by the general formula:

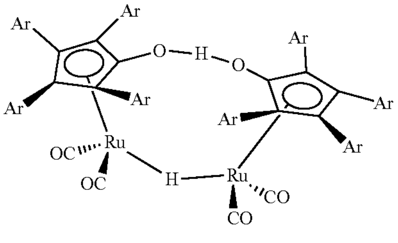

and Ar is represented by the general formula:

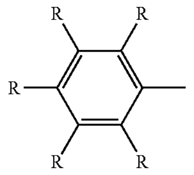

and the groups R are the same or different and are selected from H, methyl, ethyl, or a linear or branched alkyl group containing from 3 to 10 carbon atoms, substituted or unsubstituted aromatic group, a carbonyl-containing group such as an ester or amido group with 2-12 carbon atoms, an amino group with 2-12 carbon atoms, alkoxy with 3-10 carbon atoms, a nitrile, fluoro, trifluoromethyl or fluorinated hydrocarbon group such as perfluorobutyl or pentaflurophenyl.

In one embodiment, the transfer hydrogenation catalyst is selected from $(Ph_4C_4CO)2H(\mu\text{-}H)(CO)4Ru2$, [(4-ClC6H4)4C4CO]2H(μ-H)(CO)4Ru2, [2,5-(C6H4)2-3,4-(4-MeOC6H4)2C4CO]2H(μ-H)(CO)4Ru2, or [2,5-(C6H4)2-3,4-(4-FC6H4)2C4CO]2H(μ-H)(CO)4Ru2.

In one embodiment, the transfer hydrogenation catalyst is a Shvo's catalyst or ((Ph4C4CO)2H(μ-H)(CO)4Ru2).

In one embodiment, the secondary alcohol and the corresponding ketone is one or more of propane-2-ol and propan-2-one, butan-2-ol and butan-2-one, pentan-2-ol and pentan-2-one, 3-methylbutan-2-ol and 3 methylbutan-2-one, pentan-3-ol and pentan-3-one, hexan-2-ol and hexan-2-one, 4-methylpentan-2-ol and 4-methylpentan-2-one, 3-methylpentan-2-ol and 3-methylpentan-2-one, 3,3-dimethylbutan-2-ol and 3,3-dimethylbutan-2-one, hexan-3-ol and hexan-3-one, 2-methylpentan-3-ol and 2-methylpentan-3-one, and cyclohexanol and cyclohexanone.

In one embodiment, the secondary alcohol and the corresponding ketone is isopropanol and acetone.

In one embodiment, the conversion of the 2,2,4,4-tetramethylcyclobutanedione (dione) is at least 50%, or at least 70%, or at least 90%.

In one embodiment, the selectivity to 2,2,4,4-tetramethylcyclo-butane-1,3-diol (TMCD) is at least 30%, or at least 60%.

DETAILED DESCRIPTION OF THE INVENTION

Figure 1:
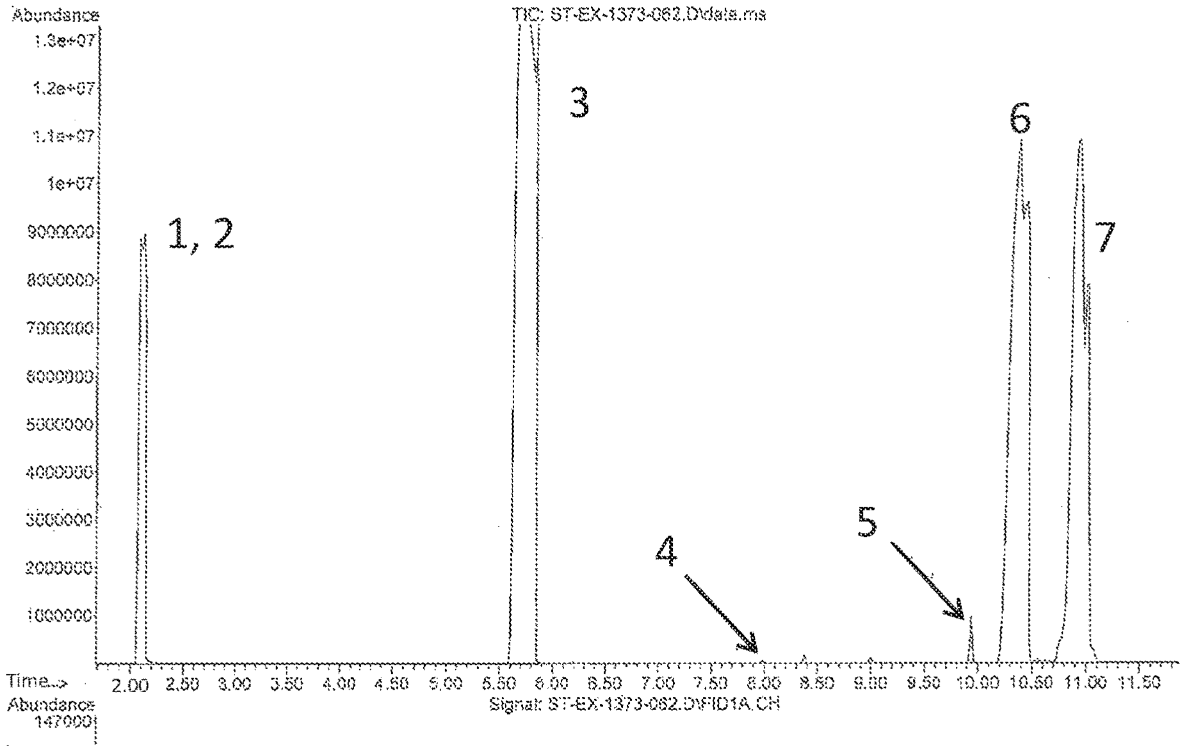
FIG. 1 is a GC/MS chromatogram of a reaction product.

In the present disclosure, it has been discovered that a ruthenium-containing homogeneous catalyst can be used to catalyze a transfer hydrogenation (TH) reaction between a dione and a secondary alcohol to give a highly selective reduction of the dione, along with the coproduction of the corresponding ketone.

In one embodiment, the present disclosure provides a process for preparing 2,2,4,4-tetramethylcyclobutane-1,3-diol. The process comprises contacting 2,2,4,4-tetramethylcyclobutanedione with a secondary alcohol in the presence of a ruthenium-containing homogeneous catalyst or a Shvo's catalyst.

In one embodiment of the present disclosure, it has been discovered that Shvo's catalyst 1 can be used to catalyze a transfer hydrogenation (TH) reaction between 2,2,4,4-tetramethylcyclobutanedione (dione) and isopropyl alcohol (iPrOH) to give highly selective reduction of the dione, along with the coproduction of acetone, eqs 1-2.

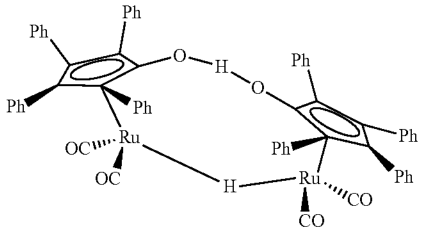

1

(1)

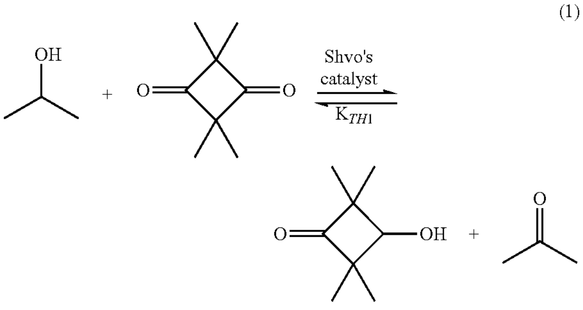

ketol (2)

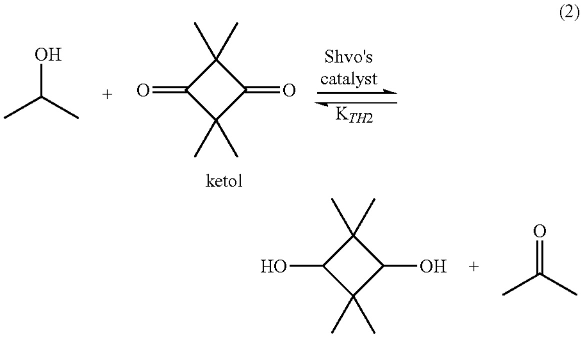

ketol

TMCD

In one embodiment of the present disclosure, the process is as follows:

(i.a) the transfer-hydrogenation of 2,2,4,4-tetramethylcyclobutanedione using isopropanol as the hydrogen donor with the production of the ketol and acetone, and (ii.a) the transfer-hydrogenation of the ketol with addition of isopropanol with the production of the TMCD and acetone In one embodiment of the present disclosure, the process requires the following:

(iii) the transfer-hydrogenation of 2,2,4,4-tetramethylcyclobutanedione using a secondary alcohol as the hydrogen donor with the production of the TMCD and the corresponding ketone.

In one embodiment of the present disclosure, the list of possible secondary alcohols and corresponding ketones is as shown below.

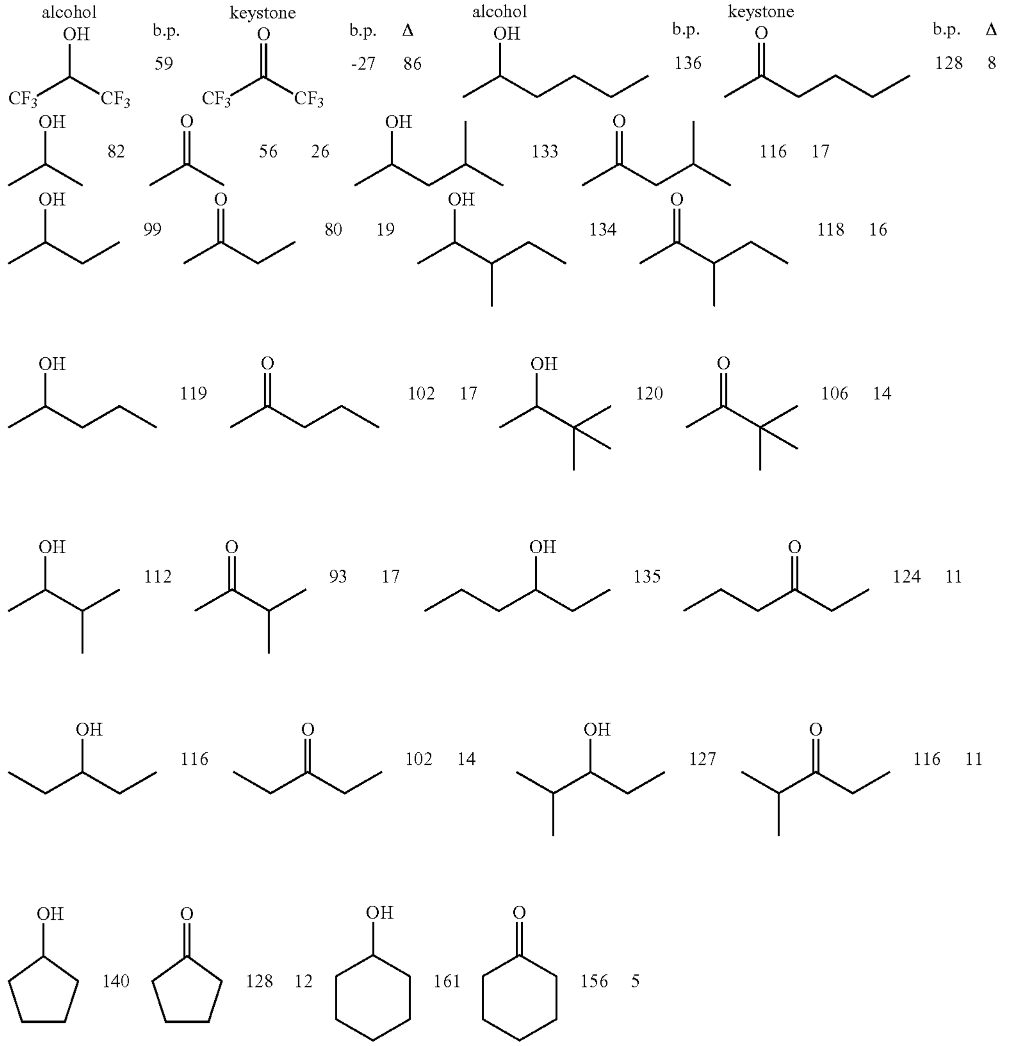

Boiling points of alcohols, their corresponding ketones and the difference (Δ) in their boiling points.

One embodiment of the present disclosure is a process for the producing 2,2,4,4-tetramethylcyclobutane-1,3-diol comprising:

(i) contacting 2,2,4,4-tetramethylcyclobutanedione with a secondary alcohol in the presence of a transfer hydrogenation catalyst to produce 3-hydroxy-2,2,4,4-tetramethylcyclobutanone and the corresponding ketone derived from the secondary alcohol; and (ii) contacting the 3-hydroxy-2,2,4,4-tetramethylcyclobutanone with a secondary alcohol in the presence of a transfer hydrogenation catalyst to produce 2,2,4,4-tetramethylcyclobutane-1,3-diol and the corresponding ketone derived from the secondary alcohol, wherein the ketone is optionally removed by reactive distillation.

In one embodiment, the transfer hydrogenation catalyst is a ruthenium complex compound.

In one embodiment, the transfer hydrogenation catalyst is one or more of $H_2Ru(PPh_3)_4$, $Ru_3(CO)_{12}$, $(Ar_4C_4CO)Ru(CO)_3$ and $(Ar_4C_4CO)_2H(\mu\text{-}H)(CO)_4Ru_2$, wherein $(Ar_4C_4CO)Ru(CO)_3$ is represented by the general formula:

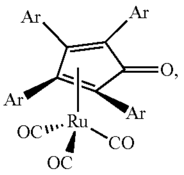

and Ar is represented by the general formula:

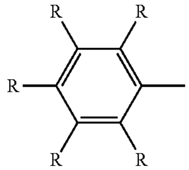

and the groups R are the same or different and are selected from H, methyl, ethyl, or a linear or branched alkyl group containing from 3 to 10 carbon atoms, substituted or unsubstituted aromatic group, a carbonyl-containing group such as an ester or amido group with 2-12 carbon atoms, an amino group with 2-12 carbon atoms, alkoxy with 3-10 carbon atoms, a nitrile, fluoro, trifluoromethyl or fluorinated hydrocarbon group such as perfluorobutyl or pentafluorophenyl;

and wherein $(Ar_4C_4CO)_2H(\mu\text{-}H)(CO)_4Ru_2$ is represented by the general formula:

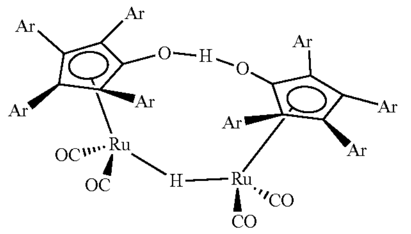

and Ar is represented by the general formula:

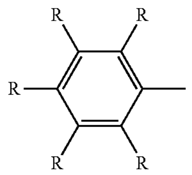

and the groups R are the same or different and are selected from H, methyl, ethyl, or a linear or branched alkyl group containing from 3 to 10 carbon atoms, substituted or unsubstituted aromatic group, a carbonyl-containing group such as an ester or amido group with 2-12 carbon atoms, an amino group with 2-12 carbon atoms, alkoxy with 3-10 carbon atoms, a nitrile, fluoro, trifluoromethyl or fluorinated hydrocarbon group such as perfluorobutyl or pentafluorophenyl.

In one embodiment, the transfer hydrogenation catalyst is selected from (Ph4C4CO)2H(μ-H)(CO)4Ru2, [(4-ClC6H4)4C4CO]2H(μ-H)(CO)4Ru2, [2,5-(C6H4)2-3,4-(4-MeOC6H4)2C4CO]2H(μ-H)(CO)4Ru2, or [2,5-(C6H4)2-3,4-(4-FC6H4)2C4CO]2H(μ-H)(CO)4Ru2.

In one embodiment, the transfer hydrogenation catalyst is ((Ph4C4CO)2H(μ-H)(CO)4Ru2).

In one embodiment, the secondary alcohol and the corresponding ketone is one or more of propane-2-ol and propan-2-one, butan-2-ol and butan-2-one, pentan-2-ol and pentan-2-one, 3-methylbutan-2-ol and 3 methylbutan-2-one, pentan-3-ol and pentan-3-one, hexan-2-ol and hexan-2-one, 4-methylpentan-2-ol and 4-methylpentan-2-one, 3-methylpentan-2-ol and 3-methylpentan-2-one, 3,3-dimethylbutan-2-ol and 3,3-dimethylbutan-2-one, hexan-3-ol and hexan-3-one, 2-methylpentan-3-ol and 2-methylpentan-3-one, and cyclohexanol and cyclohexanone. In one embodiment, the secondary alcohol and the corresponding ketone is isopropanol and acetone.

In one embodiment, the conversion of the 2,2,4,4-tetramethylcyclobutanedione is at least 50%, or at least 70%, or at least 90%.

In one embodiment, the selectivity of 2,2,4,4-tetramethylcyclobutane-1,3-diol is at least 30% or least 60%.

In one embodiment, the process of the present disclosure comprises contacting a dione with a secondary alcohol at an alcohol-to-dione molar ratio of greater than 1:1 and up to 50:1 in the presence of a ruthenium-containing homogeneous catalyst at conditions effective to produce the diol.

In one embodiment, the process of the present disclosure is performed with isopropanol-to-2,2,4,4-tetramethylcyclobutanedione molar ratio of greater than 1:1 and up to 50:1.

In one embodiment, an excess of the secondary alcohol or isopropanol is used to maximize conversion of dione to TMCD. In some embodiments, the isopropanol-to-2,2,4,4-tetramethylcyclobutanedione molar ratios include 1:1 to 50:1, 2:1 to 25:1, 3:1 to 25:1, 4:1 to 25:1, 8:1 to 25:1, 12:1 to 25:1, 16:1 to 25:1, 2:1 to 24:1, 3:1 to 24:1, 4:1 to 24:1, 8:1 to 24:1, 12:1 to 24:1, 16:1 to 24:1, 2:1 to 20:1, 3:1 to 20:1, 4:1 to 20:1, 8:1 to 20:1, 12:1 to 20:1, 16:1 to 20:1, 2:1 to 16:1, 3:1 to 16:1, 4:1 to 16:1, 8:1 to 16:1, and 12:1 to 16:1.

In one embodiment, the secondary alcohols useful in the process of the present disclosure are not particularly limiting. For example, in one embodiment, the secondary alcohol can be one or more of propane-2-ol, butan-2-ol, pentan-2-ol, 3-methylbutan-2-ol, pentan-3-ol, hexan-2-ol, 4-methylpentan-2-ol, 3-methylpentan-2-ol, 3,3-dimethylbutan-2-ol, hexan-3-ol, 2-methylpentan-3-ol, or cyclohexanol. In one embodiment, the secondary alcohols may have 1 to 12 carbon atoms, which may be straight-chain, branched, alicyclic, or aromatic. In one embodiment, suitable secondary alcohols include n-propanol, i-propanol, n-butanol, i-butanol, and 2-ethylhexanol. In one embodiment, the alcohol is i-butanol or isobutanol. In one embodiment, the alcohol is i-propanol or isobutanol.

In one embodiment, the process of the present disclosure is carried out in the presence of a transfer hydrogenation catalyst. In one embodiment, a ruthenium complex compound is used as a catalyst. In one embodiment, the catalyst is Shvo's catalyst 1.

By "ruthenium complex compound", it is meant a complex compound containing one or more ruthenium atoms and one or more ligands linked by direct metal-ligand bonding. The formal oxidation number of the ruthenium atom, and the type and quantity of groups serving as the ligand are not particularly limiting. Examples of such ligands include carbon monoxide, phosphines, hydrides, and substituted cyclopentadienones. Substituted cyclopentadienones are preferred ligands.

In one embodiment, examples of suitable RuCCs include $H_2Ru(PPh_3)_4$, $Ru_3(CO)_{12}$, (Ar4C4CO)Ru(CO)3 and (Ar4C4CO)2H(μ-H)(CO)4Ru2, $(Ph_4C_4CO)Ru(CO)_3$, $[(4\text{-}ClC_6H_4)_4C_4CO]Ru(CO)_3$, $[2,5\text{-}(C_6H_4)_2\text{-}3,4\text{-}(4\text{-}MeOC_6H_4)_2C_4CO]Ru(CO)_3$, $[2,5\text{-}(C_6H_4)_2\text{-}3,4\text{-}(4\text{-}FC_6H_4)_2C_4CO]Ru(CO)_3$, $(Ph_4C_4CO)_2H(\mu\text{-}H)(CO)_4Ru_2$, $[(4\text{-}ClC_6H_4)_4C_4CO]2H(\mu\text{-}H)(CO)_4Ru_2$, $[2,5\text{-}(C_6H_4)_2\text{-}3,4\text{-}(4\text{-}MeOC_6H_4)_2C_4CO]_2H(\mu\text{-}H)(CO)_4Ru_2$, and $[2,5\text{-}(C_6H_4)_2\text{-}3,4\text{-}(4\text{-}FC_6H_4)_2C_4CO]_2H(\mu\text{-}H)(CO)_4Ru_2$. These compounds can be synthesized using well-known methods (e.g., N. Menashe et al., *Organometallics*, Vol. 10, p. 3885 (1991)).

In one embodiment, the $(Ar_4C_4CO)Ru(CO)_3$ is represented by the general formula:

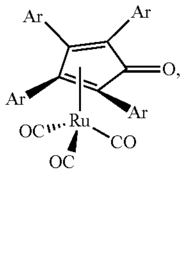

and Ar is represented by the general formula:

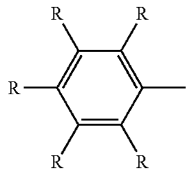

and the groups R are the same or different and are selected from H, methyl, ethyl, or a linear or branched alkyl group containing from 3 to 10 carbon atoms, substituted or unsubstituted aromatic group, a carbonyl-containing group such as an ester or amido group with 2-12 carbon atoms, an amino group with 2-12 carbon atoms, alkoxy with 3-10 carbon atoms, a nitrile, fluoro, trifluoromethyl or fluorinated hydrocarbon group such as perfluorobutyl or pentafluorophenyl;

In one embodiment, $(Ar_4C_4CO)_2H(\mu\text{-}H)(CO)_4Ru_2$ is represented by the general formula:

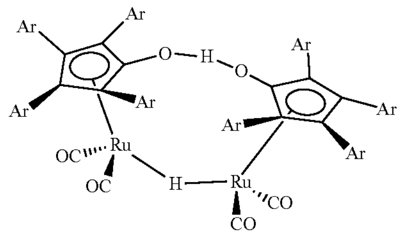

and Ar is represented by the general formula:

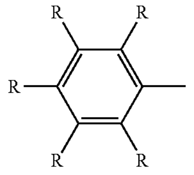

and the groups R are the same or different and are selected from H, methyl, ethyl, or a linear or branched alkyl group containing from 3 to 10 carbon atoms, substituted or unsubstituted aromatic group, a carbonyl-containing group such as an ester or amido group with 2-12 carbon atoms, an amino group with 2-12 carbon atoms, alkoxy with 3-10 carbon atoms, a nitrile, fluoro, trifluoromethyl or fluorinated hydrocarbon group such as perfluorobutyl or pentafluorophenyl.

In one embodiment, the amount of catalyst used can range from $10^{-7}$:1 to 1:1 (molar ratio) with respect to the dione. In one embodiment, the amount of catalyst used can range from $10^{-3}$:1 to 0.01:1 (molar ratio) with respect to the dione. In one embodiment, the catalyst concentration is from about 0.001 mole percent to 10 mol percent based on the concentration of the dione. In one embodiment, the catalyst concentration, based on the concentration of the dione, is from about 0.001 mole percent to 9 mol percent, or is from about 0.001 mole percent to 5 mol percent, or is from about 0.001 mole percent to about 1 mol percent, or is from about 0.01 mole percent to about 10 mol percent or is from about 0.01 mole percent to about 5 mol percent, or is from about 0.01 mole percent to about 1 mol percent, or is from about 0.1 mole percent to about 10 mol percent, or is from about 0.1 mole percent to about 5 mol percent, or is from about 0.1 mole percent to about 1 mol percent.

After the reaction, the catalyst can be separated from the products by distillation, extraction, adsorption, or other ordinary methods, and reused.

The process of the present disclosure can be carried out without a solvent. But if the RuCC has low solubility in the reaction medium comprising the dione and the alcohol, the reaction can be carried out in a suitable solvent in order to dissolve the RuCC, or as otherwise needed. Examples of suitable solvents include hydrocarbons such as hexane, benzene, and toluene; ethers such as diethyl ether, dimethoxyethane, tetrahydrofuran, and dioxanes; and esters such as ethyl acetate, butyl acetate, and 2-ethylhexyl acetate.

The reaction is typically carried out by introducing the dione, the secondary alcohol, and the catalyst into a vessel, and then mixing the contents. In one embodiment, the reaction is carried out by introducing the dione, the secondary alcohol, and a transfer hydrogenation catalyst into a vessel, and then mixing the contents. In one embodiment, the reaction temperature can range from 50 to 300° C., or from 50 to 200° C., or from 60 to 200° C., or from 70 to 200° C., or from 80 to 200° C., or from 90 to 200° C., or from 100 to 200° C., or from 150 to 200° C., or from 50 to 150° C., or from 100 to 150° C., or from 50 to 100° C. In one embodiment, the process temperature ranges from about 50° C. to about 300° C. In one embodiment, the process temperature ranges from about 50° C. to about 200° C.

The reaction pressure is not particularly limiting. The reaction may be carried out at atmospheric pressure or at elevated pressure. In one embodiment, the reaction is carried out in an inert atmosphere. In one embodiment, the reaction is carried out under nitrogen pressure to the keep the secondary alcohol in a liquid state. In one embodiment, the reaction is carried out under at least 200 psig of inert pressure (to keep the secondary alcohol in a liquid state).

In one embodiment, the reaction time depends on the reaction temperature and catalyst concentration, and the reaction time can range, for example, from 0.1 to 10 hours, or from 0.5 to 3 hours, or from 5 minutes to 5 hours, or from 5 minutes to 4 hours, or from 5 minutes to 3 hours, or from 5 minutes to 2 hours, or from 5 minutes to 1 hour, or from 5 minutes to 30 minutes, or from 30 minutes to 5 hours, or from 30 minutes to 4 hours, or from 30 minutes to 2 hours, or from 30 minutes to 1 hour.

In one embodiment of the process of the present disclosure is carried at isopropanol to dione molar ratio of greater than 1:1 and up to 50:1 in the presence of a transfer hydrogenation catalyst at conditions effective to produce the corresponding ketone and TMCD. In one embodiment, the concentration of the isopropanol to dione is from a molar ratio of 1:1 to 40:1. In one embodiment, the concentration of the isopropanol to dione is from a molar ratio of 1:1 to 30:1. In one embodiment, the concentration of the isopropanol to dione is from a molar ratio of 1:1 to 20:1. In one embodiment, the concentration of the isopropanol to dione is from a molar ratio of 1:1 to 10:1. In one embodiment, the concentration of the isopropanol to dione is from a molar ratio of 1:1 to 5:1. In one embodiment, the concentration of the isopropanol to dione is from a molar ratio of 1:1 to 2.5:1.

In one embodiment, the process of the disclosure is capable of converting the dione at a degree of conversion of at least 50%; or at least 55%, or at least 60%, or at least 65%, or at least 70%, or at least 75%, or at least 80%, or at least 85%, or at least 90%, or at least 95%. In one embodiment, the conversion of the dione is at least 70%. In one embodiment, the conversion of the dione is at least 80%. In one embodiment, the conversion of the dione is at least 90% in some embodiments, the degree of conversion is determined by the following equation:

$$\%\ \text{Conversion} = \frac{\text{moles of dione consumed}}{\text{moles of dione fed}} \times 100$$

In some embodiments, the process of the present disclosure can have selectivity to TMCD of at least 30%, or at least 40%, or at least 50%, or at least 60%, or at least 70%, or at least 80% or at least 90% or at least 95%. In one embodiment, the selectivity of TMCD is at least 30%. In one embodiment, the selectivity of TMCD is at least 50%. In one embodiment, the selectivity of TMCD is at least 60%.

The sensitivity of dione to heterogenous catalysis is illustrated by example Example 1. A TH reaction of iPrOH and dione was attempted in the presence of 7 wt % Ru/C (BASF) heterogeneous catalyst. The experiment was performed at 165° C. for 3 h with sampling. Analysis by GC (see Table 1, Example 1) showed that only very small amounts of the desired ketol and/or TMCD products were formed. The major product of the reaction was diisopropylketone (DIPK), apparently formed by the decarbonylation of dione reactant catalyzed by the ruthenium catalyst (eq. 3).

(3)

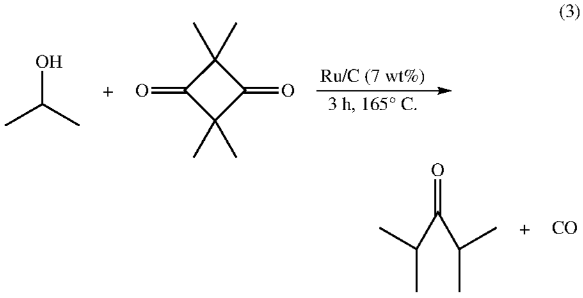

DIPK

In one embodiment of a TH reaction of dione with iPrOH (1:4 mole ratio) using a homogeneous catalyst, conducted using Shvo's catalyst 1. The experiment was performed at 150° C. for 3 h using 0.1 mol % catalyst (with respect to dione). After 3 h of reaction the reaction product was analyzed using Gas Chromatography-Mass Spectrometry (GC-MS). The chromatogram (FIG. 1, Example 3) shows that the reaction proceeded cleanly to make acetone and a mixture of ketol and TMCD products (eq. 4). The final reaction product was also analyzed for traces of isobutyric acid using a ppm GC method. The level of isobutyric acid in the final reaction product was below the detection limit (50 ppm).

(4)

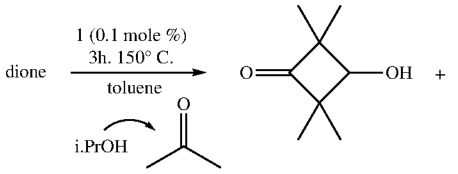

-continued

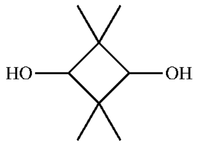

Figure 2:
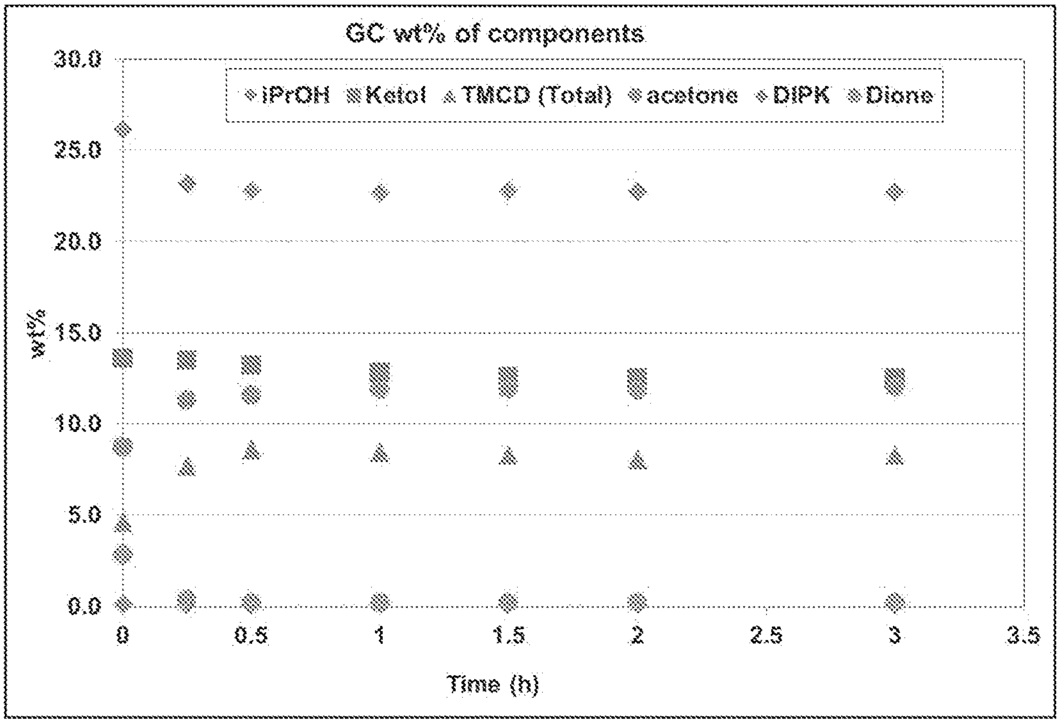
FIG. 2 is a TH kinetic studies at 150° C. (Note: there was a 12 min heat-up time before the t=0 min sample, see example 4 in the experimental section).

A TH kinetic study was conducted at 150° C. using 4:1 mole ratio of iPrOH and dione feeds and 0.1 mol % of Shvo's catalyst. The reaction reached equilibrium in less than 1 h (FIG. 2, Example 4). Because the reaction is equilibrium limited, the conversion can benefit by removal of the volatile acetone product (reactive distillation). The combined selectivities to Ketol and TMCD products remain very high during the reaction (Table 3, Example 4). In addition the selectivity of the conversion of isopropanol to acetone remained over 97%.

Figure 3:
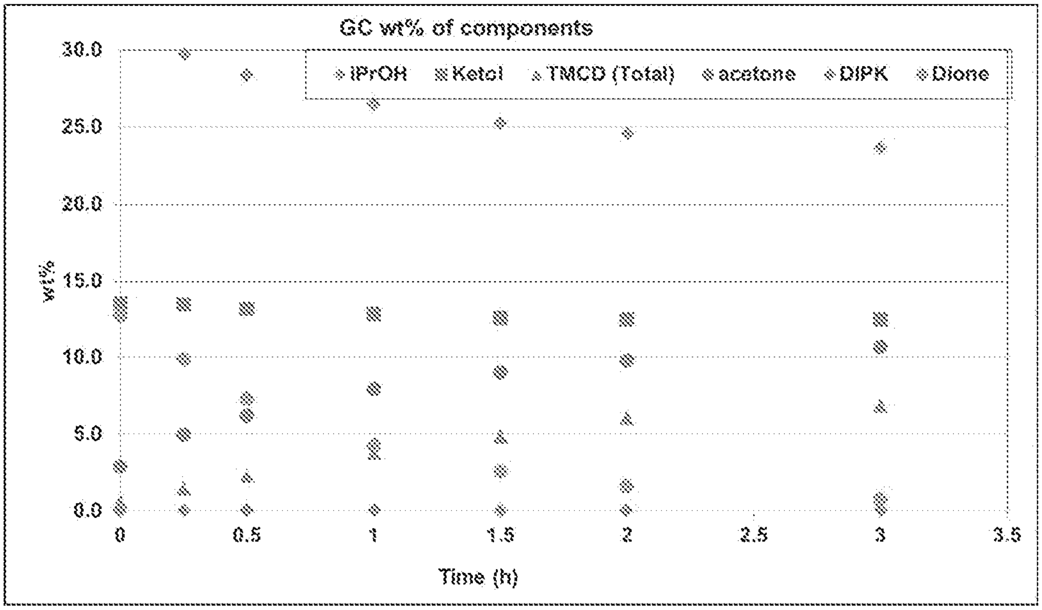
FIG. 3 is a TH kinetic studies at 100° C. (Note: there was a 12 min heat-up time before the t=0 min sample was taken.) The cis/trans ratio of TMCD remained around 1.3 during the reaction (see example 5 in the experimental section).

When a TH kinetic study was conducted at lower temperature, i.e. 100° C., using the same conditions as described above (4:1 mole ratio of iPrOH and dione feeds and 0.1 mol % Shvo's catalyst loading) the reaction reached equilibrium in about 2 h (FIG. 3, Example 5). This suggests that the TH reaction can be conducted at a reasonable rate at lower temperature which will be beneficial for the longevity of the catalyst.

The present disclosure includes and expressly contemplates any and all combinations of embodiments, features, characteristics, parameters, and/or ranges disclosed herein. That is, the present disclosure may be defined by any combination of embodiments, features, characteristics, parameters, and/or ranges mentioned herein.

As used herein, the indefinite articles "a" and "an" mean one or more, unless the context clearly suggests otherwise. Similarly, the singular form of nouns includes their plural form, and vice versa, unless the context clearly suggests otherwise.

As used herein, the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

While attempts have been made to be precise, the numerical values and ranges described herein should be considered to be approximations (even when not qualified by the term "about"). These values and ranges may vary from their stated numbers depending upon the desired properties sought to be obtained by the present disclosure as well as the variations resulting from the standard deviation found in the measuring techniques. Moreover, the ranges described herein are intended and specifically contemplated to include all sub-ranges and values within the stated ranges. For example, a range of 50 to 100 is intended to describe and include all values within the range including sub-ranges such as 60 to 90 and 70 to 80.

The content of all documents cited herein, including patents as well as non-patent literature, is hereby incorporated by reference in their entirety. To the extent that any incorporated subject matter contradicts with any disclosure herein, the disclosure herein shall take precedence over the incorporated content.

This disclosure can be further illustrated by the following examples of preferred embodiments thereof, although it will be understood that these examples are included merely for purposes of illustration and are not intended to limit the scope of the disclosure.

Experimental

Materials: Isopropanol and toluene were obtained from Aldrich. Shvo's catalyst was obtained from Strem. 7 wt % Ru/C catalyst was obtained from BASF.

Gas Chromatographic Method. Process samples were analyzed by using an Agilent gas chromatograph Model 6890 equipped with a split/heated injector (250° C.) and a thermo couple detector (250° C.). A capillary column (30 meter×0.32 mm ID) coated with (50% methyl, 50% phenyl silicone) at 0.25 μm film thickness (such as DB-Wax or equivalent) was employed. Helium was used as the carrier gas with an initial column head pressure of 7.42 psi and an initial column flow of 1.56 mL/minute while the carrier gas linear velocity of 45 cm/second was maintained constant throughout the entire oven temperature program. The column temperature was programmed as follows: The initial oven temperature was set at 40° C. and was held for 3 minutes, the oven was ramped up to 200° C. at 8° C./minute and was held at 200° C. for 2 minutes (the total run time was 25 mins). 0.5-μl of the prepared sample solution was injected with a split ratio of 75:1. EZ-Chrom Elite chromatography data system software was used for data acquisition and data processing. The sample preparation was done by weighing 0.1 g (accurate to 0.1 mg) of sample in a GC vial and adding 1.0 mL ISTD solution (1% by volume of diethylene glycol dimethyl ether in acetonitrile) to the GC vial. The GC components of this method are shown below.

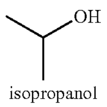

isopropanol water

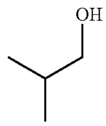

isobutanol
iBuOH

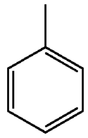

toluene

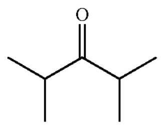

2,4-dimethyl-3-pentanone
DIPK

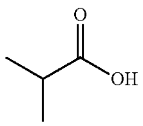

isobutyric acid
iHOBu

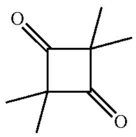

2,2,4,4-tetramethylcyclobutane
-1,3-dione
Dione

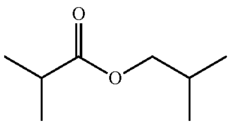

isobutyl isobutyrate
iBiB

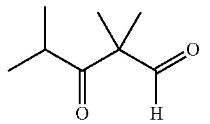

2,2,4-trimethyl-3-oxopentanal
Ketone-Aldehyde

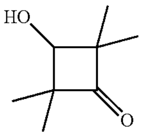

3-hydroxy-2,2,4,4-tetramethyl
cyclobutanone
Ketol

-continued

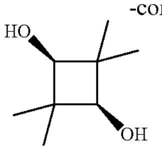

cis-2,2,4,4-tetramethyl
cyclobutane-1,3-diol
cis TMCD

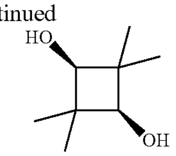

trans-2,2,4,4-tetramethyl
cyclobutane-1, 3-diol
transTMCD

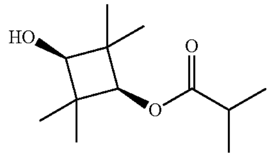

cis-3-hydroxy-2,2,4,4-tetramethyl
cyclobutyl isobutyrate
Mester1

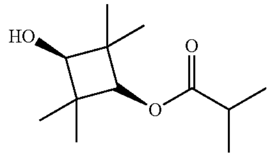

trans-3-hydroxy-2,2,4,4-tetramethyl
cyclobutyl isobutyrate
Mester2

Acetone

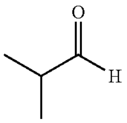

isobutyraldehyde
iHBu

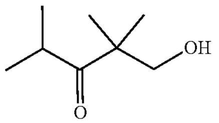

1-hydroxy-2,2,4-trimethyl
pentan-3-one
TMOP

Chemical structures of GC components analyzed by the method.

Gas Chromatographic Method (ppm isobutyric acid method): Process samples were analyzed by using an Agilent gas chromatograph Model 6890 equipped with a split/heated injector (250° C.) and a thermo couple detector (250° C.). A capillary column (30 meter×0.32 mm ID) coated with (50% vial. methyl, 50% phenyl silicone) at 0.25 μm film thickness (such as DB-Wax or equivalent) was employed. Helium was used as the carrier gas with an initial column head pressure of 7.42 psi and an initial column flow of 1.56 mL/minute while the carrier gas linear velocity of 45 cm/second was maintained constant throughout the entire oven temperature program. The column temperature was programmed as follows: The initial oven temperature was set at 40° C. and was held for 3 minutes, the oven was ramped up to 200° C. at 8° C./minute and was held at 200° C. for 2 minutes (the total run time was 25 mins). 0.5-μl of the prepared sample solution was injected with a split ratio of 75:1. EZ-Chrom Elite chromatography data system software was used for data acquisition and data processing. The sample preparation was carried out by weighing 0.1 g (accurate to 0.1 mg) of sample in a GC vial and adding 1.0 mL ISTD solution (1% by volume of diethylene glycol dimethyl ether in acetonitrile) to the GC.

EXAMPLES

Example 1. A 300 mL titanium autoclave, equipped with catalyst basket, was charged with 2.0 g (1.39 mmol) of 7 wt % Ru/C catalyst. Stainless steel packing was added to the top of the catalyst to fill the basket. The autoclave was pressurized to 500 psig with $N_2$ and then vented two times. A blowcase was charged with 31.0 g (514.78 mmol) of iPrOH, 18.0 g (128.41 mmol) of dione and 101.0 g of toluene. The autoclave was equipped with a purge system, a rotameter, a back pressure regulator (BPR) and a condenser. The blowcase was bypassed and the BPR was set at 50 psig with $N_2$. The manifold was purged three times with $H_2$. The autoclave agitator speed was set to 1000 rpm and the autoclave was pressurized to 50 psig with $H_2$. A 0.53 SCFH flow of $H_2$ was established. Once the $H_2$ flow rate was established, the autoclave was heated to 180° C. and then held at those conditions (180° C., 0.53 $H_2$ flow rate) for 1 h. While holding for 1 h, the blowcase was pressurized with ~100 psig of $N_2$ then the gas inlet valve was closed and the blowcase was heated to 175° C. After the 1 h hold, the $H_2$ flow was stopped and switched to $N_2$ (the manifold was purged three times with $N_2$) and fed with 500 sccm $N_2$ at 50 psig at 180° C. for 1 h. After the blowcase and autoclave reached the desired temperature, the blowcase was pressurized to 500 psig $N_2$. The pressure in the blowcase and the autoclave were allowed to equalize and then the blowcase was isolated from the autoclave. The material was blown from the blowcase into the autoclave and enough time was allowed for the temperature to equilibrate to 165° C. while stirring. A t=0 sample was taken and the mass recorded. The heat to the blowcase was turned off. Samples were taken at t=15 min, 30 min, 60 min, 90 min, 120 min and 180 min. After 3 h the autoclave was cooled to room temperature and depressurized. The results are shown in Table 1.

TABLE 1

Hydrogen transfer reaction of iPrOH and dione.[a]

| Time (hr) | iPrOH | Ketol | cisTMCD | transTMCD | acetone | Dione | DIPK |
|---|---|---|---|---|---|---|---|
| 0.25 | 19.80 | 0.00 | 0.20 | 0.15 | 0.01 | 0.34 | 12.14 |
| 0.5 | 19.70 | 0.00 | 0.31 | 0.20 | 0.02 | 0.35 | 12.03 |
| 1 | 19.59 | 0.00 | 0.56 | 0.39 | 0.02 | 0.34 | 11.73 |
| 1.5 | 19.28 | 0.00 | 0.00 | 0.55 | 0.03 | 0.33 | 11.42 |
| 2 | 19.12 | 0.00 | 0.00 | 0.73 | 0.04 | 0.36 | 11.19 |
| 3 | 18.43 | 0.00 | 0.00 | 1.13 | 0.05 | 0.34 | 11.19 |

[a]7 wt % Ru/C (BASF) catalyst was used. 4:1 mole ratio of iPrOH to dione was used as a feed. Reaction was conducted at 165° C. Analysis is by gas chromatography and the results are reported in wt % (see example 1 in the experimental section).

Example 2. Example 1 was repeated at 120° C. The results are shown in Table 2. Less than 4% conversion of the dione was observed.

TABLE 2

Hydrogen transfer reaction of iPrOH and dione.[a]

| Time (hr) | iPrOH | Ketol | cisTMCD | transTMCD | Acetone | DIPK | Dione |
|---|---|---|---|---|---|---|---|
| 0.25 | 20.81 | 0.33 | 0.02 | 0.02 | 0.10 | 0.010 | 12.02 |
| 0.5 | 20.64 | 0.44 | 0.02 | 0.02 | 0.12 | 0.011 | 11.83 |
| 1 | 20.55 | 0.62 | 0.02 | 0.02 | 0.12 | 0.012 | 11.70 |
| 1.5 | 20.04 | 0.74 | 0.02 | 0.02 | 0.12 | 0.013 | 11.56 |
| 2 | 20.38 | 0.84 | 0.02 | 0.02 | 0.13 | 0.014 | 11.47 |
| 3 | 20.44 | 0.86 | 0.02 | 0.02 | 0.13 | 0.014 | 11.35 |

[a]Ru/C (7 wt %, BASF) catalyst and a molar feed ratio of 4:1 iPrOH:dione was used. The reaction was conducted at 120° C. Gas chromatography analysis was used and the results are reported in wt % (see example 2 in the experimental section).

Example 3. A 100 mL titanium autoclave was charged with 20.0 g (332.1 mmol) of iPrOH, 11.6 g (82.75 mmol) of dione and 0.1 g (0.082 mmol) of Shvo's catalyst. The autoclave was pressurized with about 100 psig of $N_2$ and then vented two times. It was then pressurized with 200 psig of $N_2$ again and the closed autoclave was heated to 150° C. and kept at reaction temperature for 3 h. It was then cooled to room temperature and depressurized. The liquid product was analyzed by GC/MS chromatography and ppm level isobutyric acid GC method. The results are shown in FIG. 1.

Example 4. A 300 mL titanium autoclave was charged with 60.0 g (996.3 mmol) of iPrOH, 34.8 g (248.25 mmol) of dione (mole ratio of iPrOH to dione=4.0:1.0) and 0.3 g (0.25 mmol) of Shvo's catalyst. The autoclave was pressurized with about 100 psig of $N_2$ and then vented two times. Then it was pressurized with 200 psig of $N_2$ again and the closed autoclave was heated to 150° C. and kept at reaction temperature for 3 h. At t=0 sample was taken and the mass recorded. Samples were taken at t=15 min, 30 min, 60 min, 90 min, 120 min and 180 min. After 3 h the autoclave was cooled to room temperature and depressurized. The samples were analyzed by gas chromatography. Conversions and selectivities are summarized in Table 3.

TABLE 3

Transfer hydrogenation reactions of isopropanol and dione.[a]

| Time (hr) | % conversion of dione | % selectivity of ketol[b] | % selectivity of TMCD (cis + trans)[b] | % selectivity of acetone[b] |
|---|---|---|---|---|
| 0 | 86.1% | 75.9% | 25.7% | 99.1% |
| 0.25 | 98.2% | 66.1% | 35.4% | 97.1% |
| 0.5 | 98.9% | 62.7% | 40.2% | 96.5% |
| 1 | 99.0% | 61.6% | 40.1% | 97.6% |
| 1.5 | 99.0% | 61.1% | 39.8% | 99.1% |
| 2 | 98.9% | 60.7% | 38.8% | 98.9% |
| 3 | 98.9% | 60.8% | 39.8% | 97.6% |

[a]4:1 mole ratio of iPrOH to dione was used as a feed. 0.1 mol % Shvo's catalyst loading. The experiment was conducted at 150° C. There was a 12 min heat-up time before t = 0 min sample was taken.
[b]Selectivities were calculated as number of moles of the product in the liquid phase divided by the number of mole of reactant charged. Cis/trans ratio of TMCD remained around 1.3 during the reaction (see example 4 in the experimental section).

Example 5. Example 4 was repeated at 100° C. The results are shown in FIG. 3.

This disclosure has been described in detail with particular reference to preferred embodiments thereof, but it will be understood that variations and modifications can be effected within the spirit and scope of the invention.

We claim:

1. A process for the producing 2,2,4,4-tetramethylcyclobutane-1,3-diol comprising:

(i) contacting 2,2,4,4-tetramethylcyclobutanedione with a secondary alcohol in the presence of a transfer hydrogenation catalyst to produce 3-hydroxy-2,2,4,4-tetramethylcyclobutanone and the corresponding ketone derived from the secondary alcohol; and (ii) contacting the 3-hydroxy-2,2,4,4-tetramethylcyclobutanone with a secondary alcohol in the presence of a transfer hydrogenation catalyst to produce 2,2,4,4-tetramethylcyclobutane-1,3-diol and the corresponding ketone derived from the secondary alcohol, wherein the ketone is optionally removed by reactive distillation.

2. The process of claim 1, wherein the transfer hydrogenation catalyst is a ruthenium complex compound.

3. The process of claim 1, wherein the transfer hydrogenation catalyst is one or more of $H_2Ru(PPh_3)_4$, $Ru_3$ $(CO)_{12}$, $(Ar_4C_4CO)$ $Ru(CO)_3$ and $(Ar_4C_4CO)_2H$ (μ-H)$(CO)_4Ru_2$, and wherein $(Ar_4C_4CO)Ru(CO)_3$ is represented by the general formula:

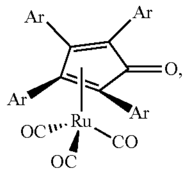

and Ar is represented by the general formula:

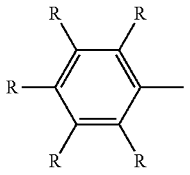

and the groups R are the same or different and are selected from H, methyl, ethyl, or a linear or branched alkyl group containing from 3 to 10 carbon atoms, substituted or unsubstituted aromatic group, a carbonyl-containing group, an amino group with 2-12 carbon atoms, alkoxy with 3-10 carbon atoms, a nitrile, fluoro, trifluoromethyl or fluorinated hydrocarbon group;

and wherein $(Ar_4C_4CO)_2H$(μ-H)$(CO)_4Ru_2$ is represented by the general formula:

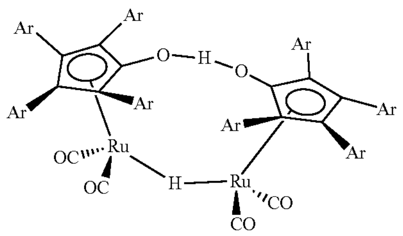

and Ar is represented by the general formula:

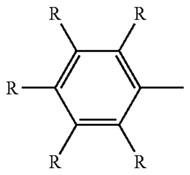

and the groups R are the same or different and are selected from H, methyl, ethyl, or a linear or branched alkyl group containing from 3 to 10 carbon atoms, substituted or unsubstituted aromatic group, a carbonyl-containing group, an amino group with 2-12 carbon atoms, alkoxy with 3-10 carbon atoms, a nitrile, fluoro, trifluoromethyl or fluorinated hydrocarbon group.

4. The process of claim 1, wherein the transfer hydrogenation catalyst is selected from (Ph4C4CO)2H(μ-H)(CO)4Ru2, [(4-ClC6H4)4C4CO]2H (μ-H)(CO)4Ru2, [2,5-(C6H4)2-3,4-(4-MeOC6H4)2C4CO]2H (μ-H)(CO)4Ru2, or [2,5-(C6H4)2-3,4-(4-FC6H4)2C4CO]2H (μ-H)(CO)4Ru2.

5. The process of claim 1, wherein the transfer hydrogenation catalyst is ((Ph4C4CO)2H(μ-H)(CO)4Ru2).

6. The process of claim 1, wherein the secondary alcohol and the corresponding ketone is one or more of propane-2-ol and propan-2-one, butan-2-ol and butan-2-one, pentan-2-ol and pentan-2-one, 3-methylbutan-2-ol and 3 methylbutan-2-one, pentan-3-ol and pentan-3-one, hexan-2-ol and hexan-2-one, 4-methylpentan-2-ol and 4-methylpentan-2-one, 3-methylpentan-2-ol and 3-methylpentan-2-one, 3,3-dimethylbutan-2-ol and 3,3-dimethylbutan-2-one, hexan-3-ol and hexan-3-one, 2-methylpentan-3-ol and 2-methylpentan-3-one, and cyclohexanol and cyclohexanone.

7. The process of claim 1, wherein the secondary alcohol and the corresponding ketone is isopropanol and acetone.

8. The process of claim 1, wherein the conversion of the 2,2,4,4-tetramethylcyclobutanedione is at least 50%.

9. The process of claim 1, wherein the conversion of the 2,2,4,4-tetramethylcyclobutanedione is at least 70%.

10. The process of claim 1, wherein the conversion of the 2,2,4,4-tetramethylcyclobutanedione is at least 90%.

11. The process of claim 1, wherein the selectivity of 2,2,4,4-tetramethylcyclobutane-1,3-diol is at least 30%.

12. The process of claim 1, wherein the selectivity 2,2,4,4-tetramethylcyclobutane-1,3-diol is at least 60%.

13. The process of claim 1, wherein the process temperature ranges from about 50° C. to about 300° C. or from about 50° C. to about 200° C.

14. The process of claim 1, wherein the process is under at least 200 psig of nitrogen pressure to the keep the secondary alcohol in a liquid state.

15. The process of claim 1, wherein the process time is from 5 minutes to 5 hours.

16. The process of claim 1, wherein the catalyst concentration is from about 0.001 mole percent to 10 mol percent based on the concentration of the 2,2,4,4-tetramethylcyclobutanedione.

17. The process of claim 1, wherein the concentration of the secondary alcohol to 2,2,4,4-tetramethylcyclobutanedione is from a mole ratio of 1:1 to 50:1.

18. The process of claim 1, wherein the concentration of the secondary alcohol to 2,2,4,4-tetramethylcyclobutanedione is from a mole ratio of 1:1 to 20:1.

19. The process of claim 1, wherein the concentration of the secondary alcohol to 2,2,4,4-tetramethylcyclobutanedione is from a mole ratio of 1:1 to 10:1.

20. The process of claim 1, wherein the concentration of the secondary alcohol to 2,2,4,4-tetramethylcyclobutanedione is from a mole ratio of 1:1 to 5:1.

* * * * *